(12) United States Patent
Hoogenakker et al.

(10) Patent No.: US 9,492,646 B2
(45) Date of Patent: Nov. 15, 2016

(54) APPLICATOR AND METHOD FOR DISPENSING A FLUID AND A PARTICULATE

(71) Applicant: Nordson Corporation, Westlake, OH (US)

(72) Inventors: Jon E. Hoogenakker, Inver Grove Heights, MN (US); Huadong Lou, Lauderdale, MN (US); Bradley D. Robb, Maple Plain, MN (US)

(73) Assignee: NORDSON CORPORATION, Westlake, OH (US)

( * ) Notice: Subject to any disclaimer, the term of this patent is extended or adjusted under 35 U.S.C. 154(b) by 275 days.

(21) Appl. No.: 13/786,901

(22) Filed: Mar. 6, 2013

(65) Prior Publication Data
US 2014/0257174 A1    Sep. 11, 2014

(51) Int. Cl.
*A61M 37/00*       (2006.01)
*A61M 11/06*       (2006.01)
(Continued)

(52) U.S. Cl.
CPC .............. *A61M 37/00* (2013.01); *A61M 11/06* (2013.01); *A61M 13/00* (2013.01); *B05B 7/1486* (2013.01); *B05B 15/066* (2013.01); *A61M 11/002* (2014.02); *A61M 2202/064* (2013.01); *A61M 2206/14* (2013.01)

(58) Field of Classification Search
CPC ......... A61M 5/2448; A61M 5/16827; A61M 3/005; A61M 5/2066; A61M 2039/0027; A61M 2205/3626; A61M 5/284; A61M 5/31596; A61M 5/3294; A61M 11/06; A61M 2206/14; B05B 15/00
USPC ............................. 604/164.11, 82, 87, 24, 89
See application file for complete search history.

(56) References Cited

U.S. PATENT DOCUMENTS 1,784,503 A * 12/1930 Swann ........................... 366/11
2,604,094 A    7/1952 Miller et al.
(Continued)

FOREIGN PATENT DOCUMENTS

DE    29516077 U1    2/1997
DE    10240324 A1    3/2004
(Continued)

OTHER PUBLICATIONS

European Patent Office, European Search Report in EP Application No. 14158037, Jun. 20, 2014.
(Continued)

*Primary Examiner* — Imani Hayman
*Assistant Examiner* — Hamza Darb
(74) *Attorney, Agent, or Firm* — Baker & Hostetler LLP (57) ABSTRACT

An applicator and method for dispensing a stream of a particulate and a fluid from a cannula and a mixing tip. The mixing tip includes a housing having an inlet, an outlet, and a mixing channel extending therebetween. A fin is positioned within the housing and extends along at least a portion of the mixing channel. The fin spirals about the mixing channel from the inlet toward the outlet for mixing and distributing the particulate generally uniformly within the fluid. The stream is directed into the mixing channel of the mixing tip and spiraled along the fin within the mixing channel. The spiraling increases turbulence and mixes the stream into a mixed stream of particulate and fluid. The mixed stream is discharged from the mixing tip for being dispensed onto an anatomical site.

23 Claims, 4 Drawing Sheets (51) Int. Cl.
*A61M 13/00* (2006.01)
*B05B 7/14* (2006.01)
*B05B 15/06* (2006.01)
*A61M 11/00* (2006.01)

(56) References Cited

U.S. PATENT DOCUMENTS

| | | | | |
|---|---|---|---|---|
| 4,123,800 | A | * | 10/1978 | Mazzei ........................ 366/163.2 |
| 4,521,349 | A | * | 6/1985 | Weber .................. B01F 3/04262 |
| | | | | 209/169 |
| 4,660,772 | A | * | 4/1987 | Rice ............................... 239/704 |
| 6,132,396 | A | * | 10/2000 | Antanavich et al. ............ 604/82 |
| 6,200,288 | B1 | | 3/2001 | Heaton et al. |
| 2011/0178495 | A1 | | 7/2011 | Ji |

FOREIGN PATENT DOCUMENTS

| | | |
|---|---|---|
| DE | 102004049983 A1 | 4/2006 |
| EP | 0237507 A1 | 9/1987 |
| JP | H06198223 A | 7/1994 |
| WO | 2012085600 A1 | 6/2012 |

OTHER PUBLICATIONS

European Patent Office, European Search Report in EP Application No. 13158753, Aug. 13, 2014.

* cited by examiner

APPLICATOR AND METHOD FOR DISPENSING A FLUID AND A PARTICULATE

TECHNICAL FIELD

The present invention relates generally to a mixing tip and method for dispensing a fluid and a particulate from a cannula, and more particularly, to a mixing tip configured for dispensing a gas and a particulate for use in a medical procedure.

BACKGROUND

Generally, it is well-known to dispense a particulate with a fluid for use in medical procedures. More specifically, the particulate and the fluid are separately received within a fluidization chamber for fluidizing the particulate within the fluid. Once the particulate is fluidized, the fluidized particulate and fluid are initially forced from the fluidization chamber with a generally turbulent flow under the influence of pressure and finally dispensed to beneficially affect the outcome of the medical procedure. For instance, a particulate, such as a coagulant particulate may be fluidized with a fluid, such as a gas, and applied onto an anatomical site for reducing the flow of blood by hemostatic clotting.

Figure 1:
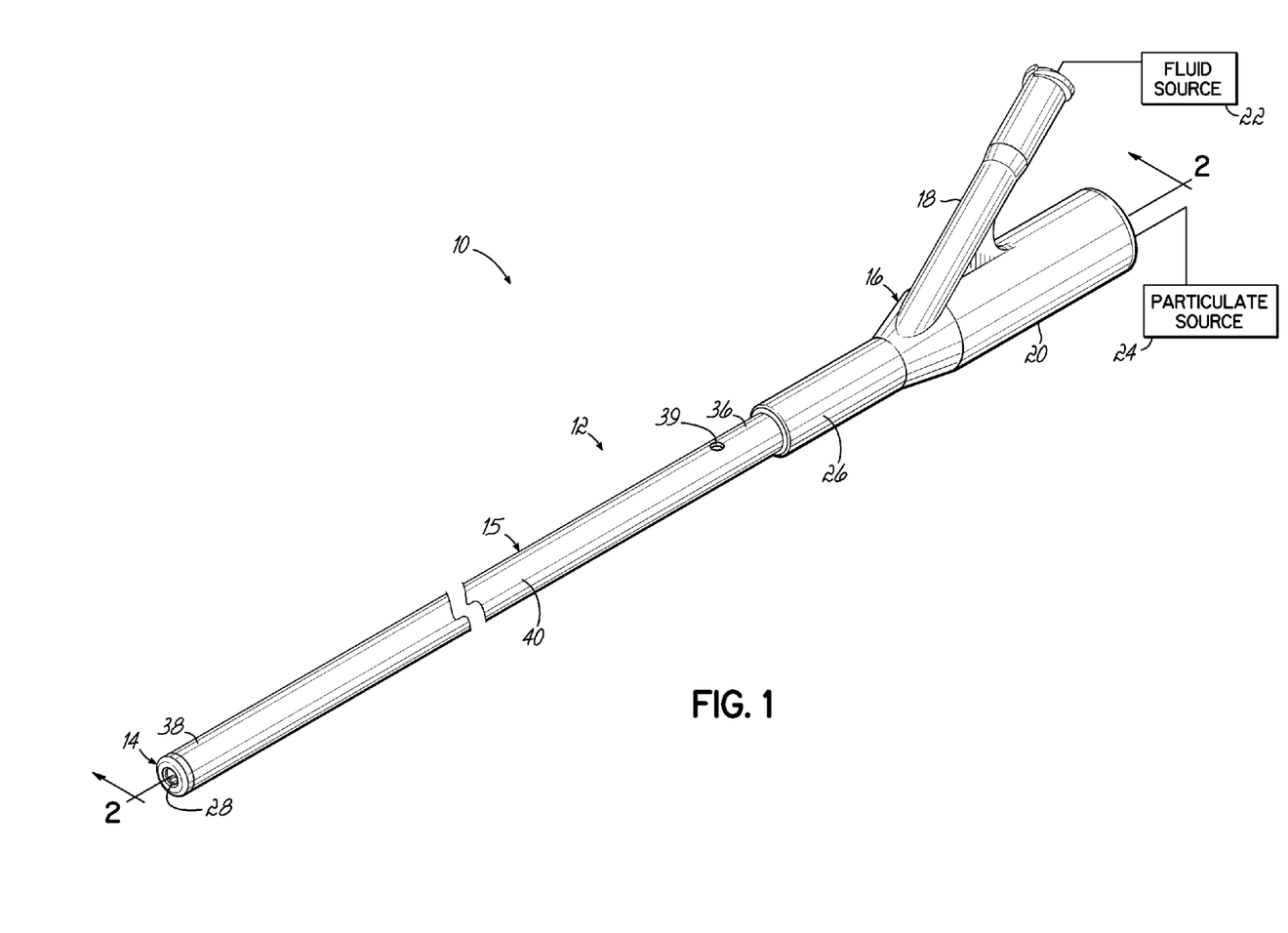

Traditionally, the fluidized coagulant particulate and gas are forced along a flow channel of an applicator for delivering the fluidized coagulant to the anatomical site. While the flow channel is useful for directing the fluidized coagulant particulate during a topical application, the flow channel may be especially useful for directing the fluidized coagulant particulate into a patient during a laparoscopic application. However, the fluidized coagulant particulate tends to stratify, or separate, from the gas due to an increasing laminar flow along the flow channel. Coagulant particulate, especially if heavy and/or sticky, tends to fall from the laminar flow and gather into a rivulet stream at a bottom of the flow channel. Thus, the rivulet stream dribbles and/or drools from the applicator while dispensing from the applicator, creating waste and mess near the anatomical site.

Moreover, the fluidized coagulant particulate directed toward the anatomical site contains variable concentrations of the coagulant particulate due to the stratification. For example, high concentrations of coagulant particulate may surge from the applicator, while low concentrations may fail to reach the anatomical site altogether. The variable concentrations of coagulant particulate may ultimately lead to wasted coagulant particulate and increased time of application to the anatomical site.

Traditional attempts for improving the distribution of the fluidized coagulant particulate to uniform density and concentration generally include increasing the amount of gas along the flow channel relative to the coagulant particulate. For example, another fluidization chamber may be added for re-fluidizing the coagulant particulate just before being discharged from the applicator. While this may effectively create a uniform density and concentration of coagulant particulate within the gas, the overall density of the coagulant particulate is reduced. Therefore, the use of the additional fluidization chamber dilutes the coagulant particulate and requires additional time and expense to complete.

There is a need for a mixing tip and method for dispensing a fluid and a particulate, such as a gas and a particulate, that addresses present challenges and characteristics such as those discussed above.

SUMMARY

An exemplary embodiment of an applicator for dispensing a generally uniform density of a particulate and fluid includes a cannula and a mixing tip. The cannula has a distal cannula end portion, a proximal cannula end portion, and a flow channel extending therethrough. The mixing tip includes a housing, an inlet, and an outlet. The inlet is positioned at a proximal end portion of the housing and configured for attaching to an applicator and receiving a stratified particulate and fluid. The outlet is positioned at a distal end portion of the housing. The mixing tip also includes a mixing channel and a first fin. The mixing channel extends through the housing from the inlet to the outlet. The first fin is positioned within the housing and extends along at least a portion of the mixing channel. In addition, the first fin is configured in a generally spiral shape about the mixing channel and positioned between the inlet and the outlet for mixing the particulate and the fluid. As such, the first fin distributes the particulate generally uniformly within the fluid for discharge from the outlet.

In one aspect, the mixing tip is operatively connected to the distal cannula end portion, and the inlet is fluidly connected to the flow channel for receiving the stratified particulate and fluid.

In use, the mixing tip dispenses a stream of fluid and particulate from the cannula during a medical procedure. The stream has a stratified particulate portion having a higher concentration of particulate than the remainder of the stream. The method includes directing the stream into the mixing channel of the mixing tip. The method also includes rotating the stream along a fluid within the mixing channel to increase turbulence and mixing the stratified particulate portion of the stream with the remainder of the stream to form a mixed stream. The mixed stream is mixed such that the particulate has a generally uniform density throughout the mixed stream of the fluid and particulate. Furthermore, the method includes discharging the mixed stream from the mixing tip.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

FIG. 1 is a perspective view of an embodiment of a device for dispensing a uniform density of a particulate and a fluid.

FIG. 2 is a cross-section view of FIG. 1 taken along section line 2-2.

FIG. 2A is a cross-section view of another embodiment of the device for dispensing the uniform density of the particulate and the fluid having a cannula with a malleable distal tube.

FIG. 3 is a front perspective view of a mixing tip according to FIG. 1.

FIG. 4 is a rear perspective view of the mixing tip shown in FIG. 3.

FIG. 5 is a section view of FIG. 3 taken along section line 5-5.

FIG. 6 is another rear perspective view of a mixing channel within the mixing tip shown in FIG. 3.

DETAILED DESCRIPTION

With reference to FIG. 1, an embodiment of a device 10 for dispensing a uniform density of a particulate and a fluid, particularly with respect to a particulate and a gas used in medical procedures. The device 10 includes an applicator 12 having a mixing tip 14. The applicator 12 has a cannula 15 and hub 16, which includes a fluid port 18 and a particulate port 20. The device 10 also includes the fluid source 22 and a particulate source 24. The fluid port 18 is operatively connected to a fluid source 22, which contains the fluid, while the particulate port 20 is operatively connected to the particulate source 24, which contains the particulate. In this respect, the fluid port 18 and particulate port 20 respectively receive the fluid and the particulate from the fluid source 22 and the particulate source 24. The hub 16 further includes an outlet port 26 connected to the cannula 15.

The mixing tip 14 includes an outlet 28 and is also connected to the cannula 15 for discharging and dispensing the fluid and particulate onto an anatomical site, which may be located anywhere on or within a patient. More particularly, the fluid is pressurized at the fluid source 22, which forces the fluid and the particulate along the cannula 15 and through the mixing tip 14. According to an exemplary embodiment, the fluid from the fluid source 22 is a gas and the particulate is a coagulant particulate for dispensing on the anatomical site. However, the applicator 12 is not intended to be limited to the exemplary embodiment described herein. While the exemplary embodiment of the applicator 12 receives gas and particulate for mixing, discharging, and dispensing, it will be appreciated that any fluid, such as a liquid or gas, and particulate, may be used in accordance with the invention during a medical procedure. In this respect, the fluid source 22 may be a gas source or a liquid source. More particularly, the mixing tip 14, the applicator 12, the gas, and the coagulant particulate may be used in a surgical procedure, such as laparoscopic or topical surgery, for improving hemostatic clotting during the procedure.

Figure 2:
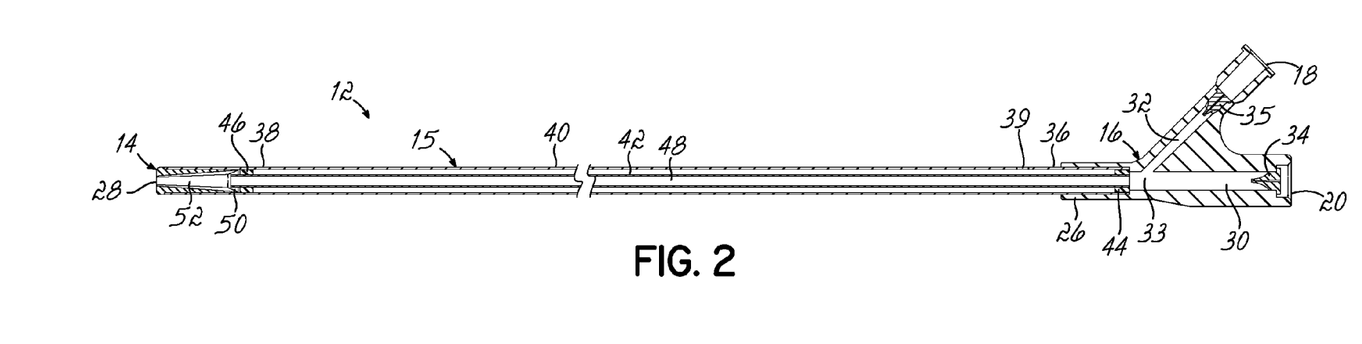
Figure 2A:
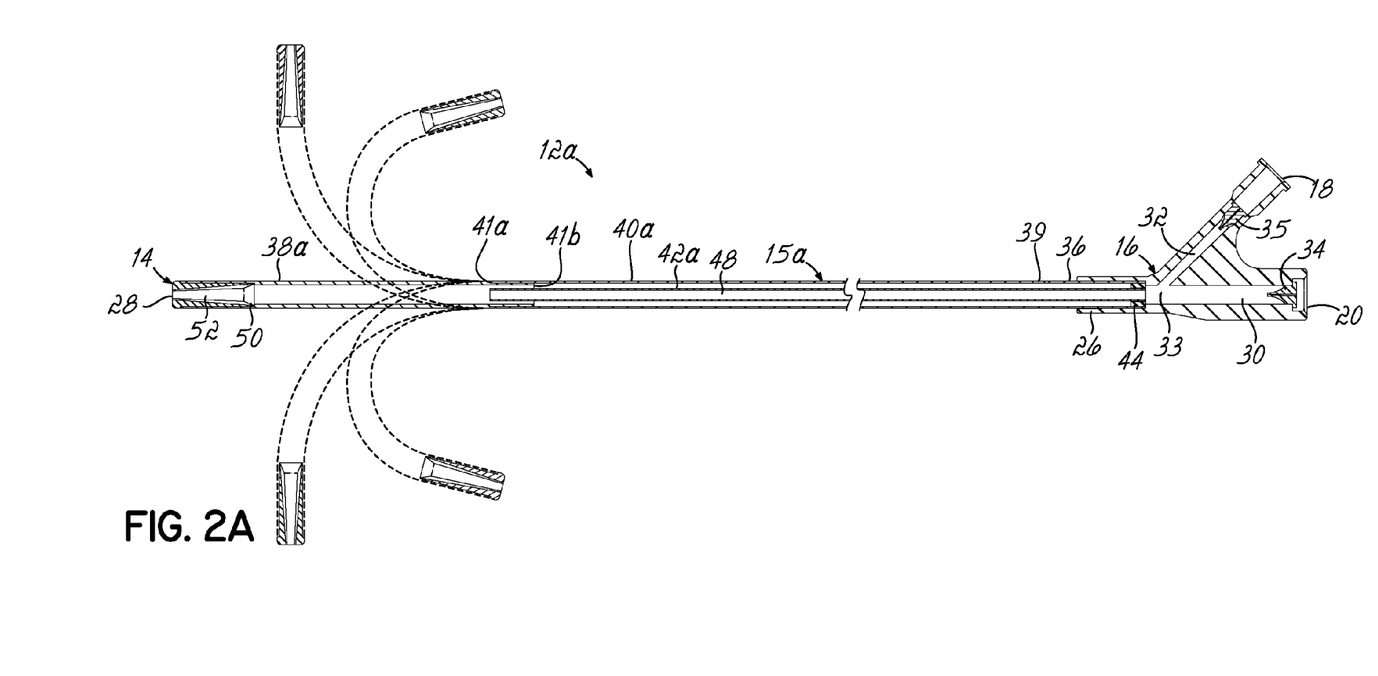
Figure 3:
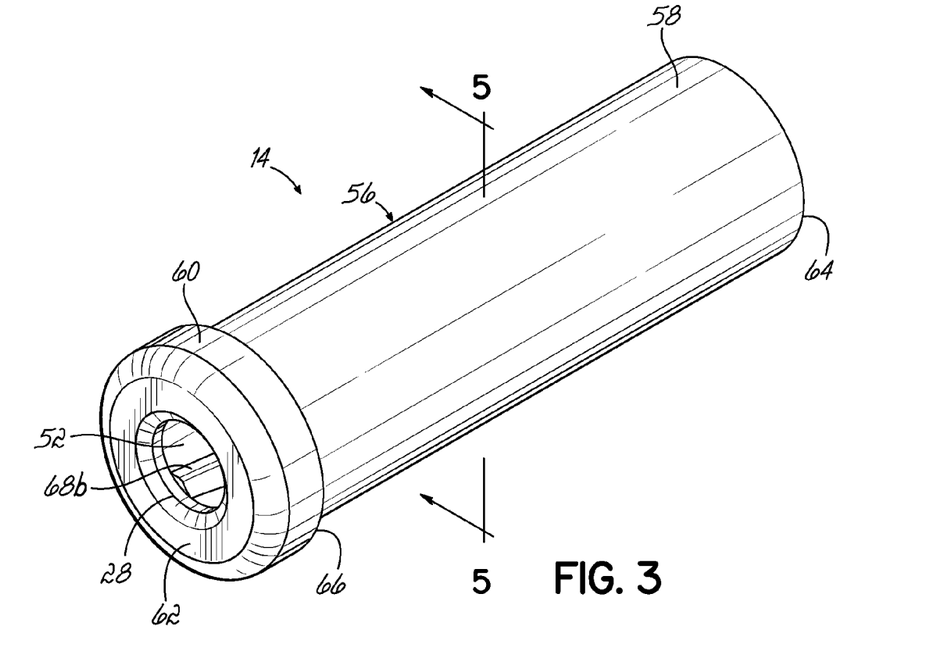
Figure 4:
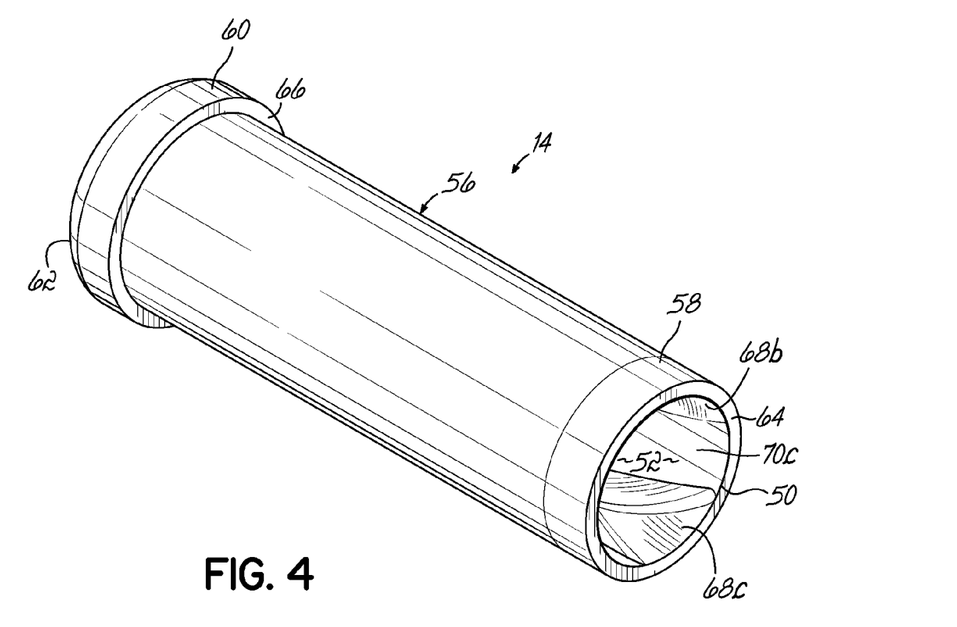
Figure 5:
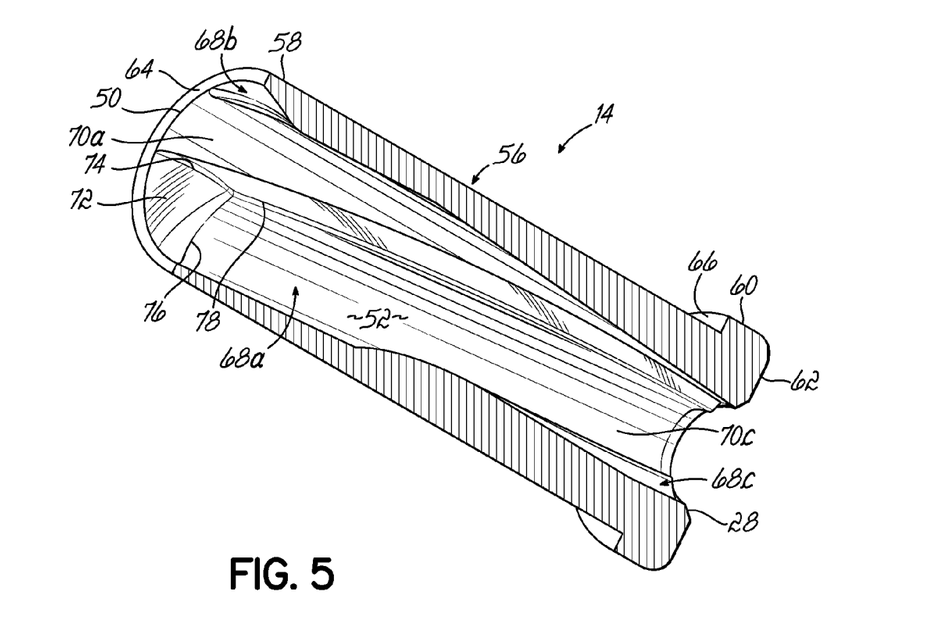
Figure 6:
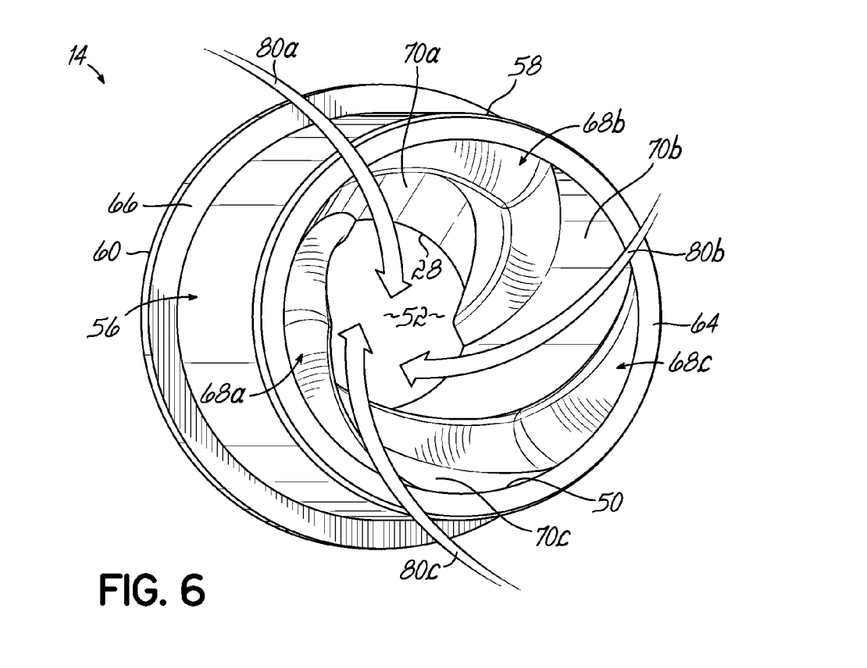

FIG. 2 shows a cross-section of the mixing tip 14 fluidly connected to the applicator 12. According to the exemplary embodiment, the hub 16 further includes a particulate channel 30, a fluid channel 32, and a fluidization chamber 33. The particulate channel 30 extends from the particulate port 20 to the fluidization chamber 33. Similarly, the fluid channel 32 extends from the fluid port 18 to the fluidization chamber 33. As such, the pressurized gas moves from the fluid port 18, along the fluid channel 32, and into the fluidization chamber 33 for drawing upon the particulate received by the particulate port 20. The particulate then moves along the particulate channel 30 and into the fluidization chamber 33. However, the particulate channel 30 also includes a particulate check valve 34 for preventing the particulate from reversing direction back toward the particulate port 20. The fluid channel 32 also includes a fluid check valve 35 for similarly preventing the fluid from reversing direction back toward the fluid port 18. Accordingly, the particulate fluidizes with the turbulent gas at the fluidization chamber 33 and, the particulate and gas flow toward the outlet port 26. Due to the relatively high turbulence of the gas within the fluidization chamber 33, the gas and the particulate are generally uniformly mixed in the fluidization chamber 33. That is, the particulate has a relatively uniform density and concentration throughout the gas as the mixture exits the fluidization chamber 33 for the outlet port 26.

The cannula 15 receives the gas and particulate from the outlet port 26 as the mixture. More particularly, the cannula 15 has a proximal cannula end portion 36 and a distal cannula end portion 38 and includes an outer tube 40 and a hypo tube 42. The hypo tube 42 is concentrically supported within the outer tube 40 by proximal and distal plugs 44, 46 respectively positioned at the upstream and distal cannula end portions 36, 38. A vent hole 39 also extends through the outer tube 40. Specifically, the vent hole 39 is positioned between the proximal and distal plugs 36, 38 for improving sterilization within the outer tube 40. In addition, the hypo tube 42 defines a flow channel 48 within the cannula 15. The cannula 15 is affixed and sealed within the hub 16 so that the outlet port 26 and the flow channel 48 are in fluid communication for receiving the relatively turbulent flow of fluidized particulate and gas.

The flow channel 48 extends through the hypo tube 42 from the proximal cannula end portion 36 toward the distal cannula end portion 38, which is configured to connect to the mixing tip 14. Generally, the mixing tip 14 includes an inlet 50, the outlet 28, and a mixing channel 52 extending therebetween. In order to couple the mixing tip 14 to the cannula 15, the outer tube 40 extends farther than the hypo tube 42. In this way, the mixing tip 14 is inserted within the outer tube 40 and the hypo tube 42 is inserted into the inlet 50 of the mixing tip 14.

As the fluidized particulate and gas move along the flow channel 48 and toward the mixing tip 14, the flow turbulence may decrease from turbulent to laminar, especially within the stream of gas and particulate immediately adjacent to the hypo tube 42. The relatively less turbulent flow and laminar flow of the fluidized particulate causes the particulate to fall from the gas and gather in a rivulet moving toward the distal cannula end portion 38 of the cannula 15. However, the mixing tip 14 is configured for mixing the particulate with the gas and creating turbulent flow in order to re-fluidize the particulate within the gas. In this way, the particulate is generally uniformly distributed throughout the discharging gas with generally uniform density and concentration for application onto the anatomical site.

FIG. 2A is another embodiment of an applicator 12*a* for use with the mixing tip 14 in which like numbers indicate like features to that of the previous embodiment. The applicator 12*a* notably includes a cannula 15*a* having a malleable distal tube 38*a*, an outer tube 40*a*, and a hypo tube 42*a*. The hypo tube 42*a* is positioned within the outer tube 40*a* and connected at the proximal end portion 36 to the hub 16 as described above. However, the outer tube 40*a* has a tube end portion 41*a* that connects to a malleable end portion 41*b* of the malleable distal tube 38*a*. As such, the malleable distal tube 38*a* and the hypo tube 42*a* collectively define the flow channel 48. In addition, the malleable distal tube 38*a* is connected to the mixing tip 14 such that the mixing channel 52 and the flow channel 48 are in fluid communication.

The malleable distal tube 38*a* may be used to position the mixing tip 14 for directing the discharging stream of the fluidized particulate. For example, laparoscopic surgery may require the use of a trocar for accessing the anatomical site within the patient. Given the limited space within the patient, accessing the anatomical site may be difficult. However, access to the anatomical site may be improved by bending the malleable distal tube 38*a* in order to position the outlet 28 of the mixing tip 14 after insertion within the trocar. For example, a medical professional, such as a doctor or nurse, may insert the mixing tip 14 and a portion of the malleable distal tube 38*a* into the trocar and bend the malleable distal tube 38*a* with a forceps to aim at the anatomical site. The operator may bend the malleable distal tube 38*a* into any desirable shape. Of course, when the medical professional releases the forceps, the malleable distal tube 38*a* maintains the desired shape. Similarly, bending the malleable distal tube 38*a* to aim the mixing tip 14 may also reduce the necessity of either moving the applicator 12a between various trocars or repositioning the patient to improve the aim of the mixing tip 14 to the anatomical site. While bending the malleable distal tube 38a may cause additional particulate to fall from the gas and stratify, the mixing tip 14 connected to the malleable distal tube 38a fluidizes the additional fallen particulate for use on the anatomical site. Thereby, the fluidized particulate discharging from the mixing tip 14 may be directed onto an otherwise unreachable or difficult to reach anatomical site with the aid of the malleable distal tube 38*a*.

The malleable distal tube 38*a* is also generally transparent for enhanced visualization of powder passing therethrough. For example, viewing the laparoscopic procedure may be difficult given the inherent challenges of operating within the patient. As such, the medical professional may lack visibility of the mixing tip 14 or portions of the anatomical site during the procedure. However, the medical professional may view the particulate passing through the transparent malleable distal tube 38*a* in order to ensure that the particulate is being applied to the anatomical site. Finally, with respect to FIGS. 2-4, the mixing tip 14 for use with both applicators 14, 14*a* is radiopaque for confirming the position of the mixing tip 14 within the patient via x-rays. Such confirmation may be particularly beneficial when performing the medical procedure with robotic applications.

The exemplary mixing tip 14 includes a generally cylindrical housing 56 having a proximal end portion 58 and a distal end portion 60. The distal end portion 60 includes a front face 62 having the outlet 28, and the proximal end portion 58 includes a rear face 64 having the inlet 50. As described above, the mixing tip 14 is configured for insertion into the outer tube 40 shown in FIG. 2. Accordingly, the proximal end portion 58 of the housing 56 is sized for insertion into the outer tube 40. Similarly, the inlet 50 is sized for receiving the hypo tube 42 therein. However, the distal end portion 60 includes a lip 66 positioned against the outer tube 40, which is indicative of proper insertion, or installation, within the cannula 15. While the exemplary embodiment shows the proximal end portion 58 and the inlet 50 frictionally engaging the respective outer tube 40 and hypo tube 42, it will be appreciated that the mixing tip 14 may be similarly connected to and sealed against the cannula 15 using luer locks, fasteners, clips, glue, or any another other structure for sealing and fluidly connecting the mixing channel 52 to the flow channel 48. Furthermore, the mixing tip 14 may be removably connected to the cannula 15 so that various other tips, such as other mixing tips, may be used with the same applicator 12 or even during the same medical procedure.

FIGS. 3-6 show the mixing tip 14 configured for mixing the fluidized particulate and gas. More particularly, the mixing tip 14 includes an exemplary embodiment of first, second, and third fins 68*a*, 68*b*, 68*c* each projecting inward from the housing 56 and into the mixing channel 52. Furthermore, the first, second, and third fins 68*a*, 68*b*, 68*c* each extend along the mixing channel 52 between the inlet 50 and the outlet 28. According to the exemplary embodiment, the first, second, and third fins 68*a*, 68*b*, 68*c* extend continuously along generally the entire mixing channel 52. However, it will be appreciated that the first, second, and third fins 68*a*, 68*b*, 68*c* may, in the alternative, extend along a portion of the mixing channel 52 between the inlet 50 and outlet 28. Similarly, the one or more of the first, second, and third fins 68*a*, 68*b*, 68*c* may, in the alternative, extend discontinuously along generally the entire mixing channel 52 or extend discontinuously along a portion of the mixing channel 52. In this respect, the fins 68*a*, 68*b*, 68*c* are not intended to be limited to the exemplary embodiment and the extension and/or continuity of the fins 68*a*, 68*b*, 68*c* may vary in accordance with the invention described herein.

Each of the first, second, and third fins 68*a*, 68*b*, 68*c* are symmetrically positioned along the mixing channel 52 and gradually spiral about the mixing channel 52 in a generally spiral shape for generating turbulence within the fluidized particulate and gas passing therethrough. According to the exemplary embodiment, each of the first, second, and third fins 68*a*, 68*b*, 68*c* spiral approximately 120 degrees from the inlet 50 toward the outlet 28. However, it will be appreciated that the desired spiraling may be used in order to generate more or less turbulence depending on the application and the types of fluid and particulate mixed in accordance with the principles of the invention described herein. Furthermore, the first, second, and third fins 68*a*, 68*b*, 68*c* define first, second, and third grooves 70*a*, 70*b*, 70*c* that spiral adjacent to each of the fins 68*a*, 68*b*, 68*c*. Generally, the grooves 70*a*, 70*b*, 70*c* work in coordination with the fins 68*a*, 68*b*, 68*c* for similarly rotating and/or agitating the stream of the fluidized particulate and gas to create additional turbulence.

With respect to FIG. 5, each of the first, second, and third fins 68*a*, 68*b*, 68*c* has a triangular profile 72 extending along the mixing channel 52. The triangular profile 72 includes a leading face 74 and a trailing face 76 projecting into the mixing channel 52 toward a fin edge 78. The leading face 74 is generally convex, and the trailing face 76 is generally concave. However, fins 68*a*, 68*b*, 68*c* may be generally any shape adapted for creating turbulence in the fluidized particulate and gas. Additional turbulence is also created by narrowing the mixing channel 52 from the inlet 50 toward the outlet 28. By narrowing the mixing channel 52, the volume of the mixing channel 52 decreases from the inlet 50 toward the outlet 28, which increases the velocity of the fluidized particulate and gas passing therethrough. In this way, the increased velocity creates additional turbulence for mixing the fluidized particulate and gas. For example, the outlet 28 has a diameter of 2 millimeters, and the inlet 50 has a diameter of more than 2 millimeters, e.g., between 2 millimeters and 3 millimeters. However, it will be appreciated that the inlet 50 and outlet 28 may vary in size for dispensing the particulate and gas, or any particulate or fluid used in a medical procedure.

FIG. 6 shows a stream of particulate and gas, indicated by first, second, and third arrows 80*a*, 80*b*, 80*c*, entering the inlet 50, moving along the mixing channel 52, and discharging from the outlet 28. As briefly described above, the fluidized particulate and gas may be stratified into a rivulet of relatively high density particulate flowing into the mixing channel 52 represented by the third arrow 80*c*. Similarly, the second arrow 80*b* may be indicative of a relatively low concentration of particulate fluidized within the gas having a relatively turbulent flow. Finally, the third arrow 80*c* may be indicative of a relatively laminar flow of relatively low concentration of particulate fluidized within the gas. As the stream of fluidized particulate and gas represented by first, second, and third arrows 80*a*, 80*b*, 80*c* is forced under pressure into the mixing channel 52, the fins 68*a*, 68*b*, 68*c* and grooves 70*a*, 70*b*, 70*c* spiral the stream in order to generate turbulence within the mixing tip 14. Additional turbulence is created as the mixing channel 52 narrows and the stream of particulate and gas increases in velocity. Finally, the rivulet at the third arrow 80*c* is guided and lifted along the third groove 70*c* and directed into the turbulence of the stream. For example, in the instance where the particulate is a coagulant particulate, the coagulant particulate re-fluidizes into a generally uniform distribution of fluidized coagulant particulate and gas mixture. Accordingly, the practitioner directs and discharges the coagulant particulate with a generally uniform density and concentration onto the anatomical site. At the anatomical site, the coagulant powder promotes the coagulation of the blood for improving the outcome of the medical procedure for the patient.

It will be appreciated that the shape and number of fins and grooves may vary to accommodate varying fluids, particulates, or medical procedures. For example, the mixing tip 14 may accommodate higher or lower density particulates by increasing or decreasing the size of the mixing channel 52. Similarly, increasing the length and/or number of fins may increase turbulence, while reducing the length and/or number of fins may decrease the likelihood of clogging the mixing channel 52. According to the exemplary embodiment, the outlet 28 is generally circular and thus, produces a generally conical plume of fluidized particulate and gas. However, the shape of the outlet 28 may be changed in order to create a generally flat or rectangular plume. For example, the flat or rectangular plume may be used for topical surgery, and the conical plume may be used for laparoscopic surgery.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. An applicator for dispensing a uniform density of a particulate and a fluid for use during a medical procedure, the applicator comprising;
    a cannula, the cannula having a distal cannula end portion and a flow channel extending therethrough;
    a mixing tip, the mixing tip operatively connected to the distal cannula end portion, the mixing tip further comprising:
        a housing having a proximal end portion and a distal end portion;
        an inlet positioned at the proximal end portion of the housing, the inlet fluidly connected to the flow channel for receiving a stratified particulate and fluid;
        an outlet positioned at the distal end portion of the housing;
        a mixing channel extending through the housing from the inlet to the outlet; and
        a first fin positioned within the housing and extending along at least a portion of the mixing channel, the first fin having a triangular cross sectional profile that receives a laminar flowing stream of the fluid and the particulate therealong and extending in a spiral shape about the mixing channel and positioned between the inlet and the outlet to increase turbulence within the stream for mixing the particulate and the fluid and distributing the particulate uniformly within the fluid for discharge from the outlet, wherein the triangular cross sectional profile includes a convex face, wherein the convex face extends along a longitudinal length of the first fin,
    wherein the applicator is discharges the particulate and the fluid during the medical procedure.

2. The applicator of claim 1 further comprising:
    a hub having a fluid inlet port and a particulate inlet port, the fluid inlet port and the particulate inlet port extending through the hub to a fluidizing chamber for receiving the fluid and the particulate; and
    the cannula having a proximal cannula end portion, the flow channel extending from the proximal cannula end portion to the distal cannula end portion, the proximal cannula end portion connected to the hub and fluidly connected to the fluidizing chamber for receiving a fluidized particulate and fluid.

3. The applicator of claim 1 wherein the mixing tip further comprises a second fin, the second fin positioned within the housing and extending along at least the portion of the mixing channel, the second fin configured in the spiral shape about the mixing channel and positioned between the inlet and the outlet for mixing the particulate and the fluid and distributing the particulate uniformly within the fluid for discharge from the outlet.

4. The applicator of claim 3 wherein the mixing tip further comprises a third fin, the third fin positioned within the housing and extending along at least the portion of the mixing channel, the third fin configured in the spiral shape about the mixing channel and positioned between the inlet and the outlet for mixing the particulate and the fluid and distributing the particulate uniformly within the fluid for discharge from the outlet,
    wherein the first, second, and third fins spiral approximately 120 degrees about the mixing channel from the inlet toward the outlet.

5. The applicator of claim 1 wherein the first fin extends along generally the entire length of the mixing channel from the inlet to the outlet.

6. The applicator of claim 1 wherein the first fin defines at least one groove within the mixing channel, the groove spiraling about the mixing channel adjacent to the first fin for receiving a laminar flowing rivulet of stratified particulate and directing the laminar flowing rivulet into a turbulent flow of fluid, wherein the laminar flowing rivulet mixes with the turbulent flow of fluid to distribute the particulate uniformly within the fluid.

7. The applicator of claim 1 wherein the cannula further includes a malleable distal tube, the mixing tip fluidly connected to the malleable distal tube for bending the malleable distal tube and aiming the mixing tip.

8. The applicator of claim 1, wherein the triangular cross-sectional profile includes a concave face, the concave face extending along the first fin between the inlet and the outlet such that a groove defined by the concave face is configured to guide and lift the particulate into the increased turbulence within the stream.

9. A mixing tip for generating uniform density of a particulate and a fluid from an applicator for use in a medical procedure, the mixing tip comprising:
    a housing having a proximal end portion and a distal end portion;
    an inlet positioned at the proximal end portion of the housing, the inlet configured for attaching to the applicator and receiving a stratified particulate and fluid;
    an outlet positioned at the distal end portion of the housing;

a mixing channel extending through the housing from the inlet to the outlet; and a first fin positioned within the housing and extending along at least a portion of the mixing channel, the first fin having a triangular cross sectional profile that receives a laminar flowing stream of the fluid and the particulate therealong and extending in a spiral shape about the mixing channel and positioned between the inlet and the outlet to increase turbulence within the stream for mixing the particulate and the fluid and distributing the particulate uniformly within the fluid for discharge from the outlet, wherein the triangular cross sectional profile includes a convex face, wherein the convex face extends along a longitudinal length of the first fin, wherein the applicator is discharges the particulate and the fluid during the medical procedure.

10. The mixing tip of claim 9 further comprising a second fin, the second fin positioned within the housing and extending along at least the portion of the mixing channel, the second fin configured in the spiral shape about the mixing channel and positioned between the inlet and the outlet for mixing the particulate and the fluid and distributing the particulate uniformly within the fluid for discharge from the outlet.

11. The mixing tip of claim 10 further comprising a third fin, the third fin positioned within the housing and extending along at least the portion of the mixing channel, the third fin configured in the spiral shape about the mixing channel and positioned between the inlet and the outlet for mixing the particulate and the fluid and distributing the particulate uniformly within the fluid for discharge from the outlet, wherein the first, second, and third fins spiral approximately degrees about the mixing channel from the inlet toward the outlet.

12. The mixing tip of claim 9 wherein the first fin extends along generally the entire length of the mixing channel from the inlet to the outlet.

13. The mixing tip of claim 9 wherein the first fin defines at least one groove within the mixing channel, the groove spiraling about the mixing channel adjacent to the first fin for receiving a laminar flowing rivulet of stratified particulate and directing the laminar flowing rivulet into a turbulent flow of fluid, wherein the laminar flowing rivulet mixes with the turbulent flow of fluid to distribute the particulate uniformly within the fluid.

14. The mixing tip of claim 9, wherein the triangular cross-sectional profile includes a concave face, the concave face extending along the first fin between the inlet and the outlet such that a groove defined by the concave face is configured to guide and lift the particulate into the increased turbulence within the stream.

15. A method of dispensing a stream of fluid and a particulate from a cannula during a medical procedure, the stream having a particulate portion having a higher concentration of particulate than the remainder of the stream, the method comprising:

directing the stream into a mixing channel of a mixing tip;

receiving the stream with a laminar flow along a triangular cross sectional profile of a fin within the mixing channel, wherein the triangular cross sectional profile includes a convex face, wherein the convex face extends along a longitudinal length of the fin;

rotating the stream along the fin within the mixing channel to increase turbulence and mix the particulate portion of the stream with the remainder of the stream to form a mixed stream such that the particulate has a uniform density throughout the mixed stream of fluid and particulate; and discharging the mixed stream from the mixing tip during the medical procedure.

16. The method of claim 15 wherein discharging the mixed stream further comprises discharging the mixed stream directly from the mixing tip.

17. The method of claim 15 further comprising positioning the mixing tip on a downstream portion of a cannula.

18. The method of claim 15 further comprising increasing the turbulence of the stream from a proximal end portion towards a distal end portion of the mixing channel within the mixing tip.

19. The method of claim 18 further comprising guiding the particulate portion along a groove within the flow channel and toward the increased turbulence of the stream.

20. The method of claim 15 further comprising increasing the velocity of the stream from a proximal end portion towards a distal end portion of the mixing channel within the mixing tip.

21. The method of claim 15 wherein the particulate is a coagulant powder and the fluid is a gas, and the method further comprises:

fluidizing the coagulant powder with the gas; and directing the coagulant powder onto an anatomical site of a patient to promote blood coagulation at the anatomical site with the coagulant powder.

22. The method of claim 15 further comprising bending a malleable distal tube fluidly connected to the mixing tip in order to aim the discharging mixed stream.

23. The method of claim 15, wherein the triangular cross-sectional profile includes a concave face, the concave face extends along the fin between the inlet and the outlet, and the method further comprises:

guiding the particulate along a groove defined by the concave face; and lifting the particulate with the groove defined by the concave face into the increased turbulence of the stream.

* * * * *